United States Patent [19]

Martin

[11] 4,402,968
[45] Sep. 6, 1983

[54] ANTIFUNGAL BENZOFURANYL IMIDAZOLE COMPOUNDS

[75] Inventor: Joseph A. Martin, Harpenden, England

[73] Assignee: Hoffmann-La Roche Inc., Nutley, N.J.

[21] Appl. No.: 268,304

[22] Filed: May 29, 1981

[30] Foreign Application Priority Data

Jun. 6, 1980 [GB] United Kingdom ................. 8018691
Mar. 2, 1981 [GB] United Kingdom ................. 8106459

[51] Int. Cl.$^3$ .................. A61K 31/415; C07D 405/12
[52] U.S. Cl. ................................. 424/273 R; 548/336; 548/341; 549/471
[58] Field of Search ..................... 548/336; 424/273 R

[56] References Cited

U.S. PATENT DOCUMENTS

| 4,045,568 | 8/1977 | Walker | 424/273 R |
|---|---|---|---|
| 4,062,966 | 12/1977 | Gymer | 548/336 X |
| 4,107,314 | 8/1978 | Cox et al. | 548/336 X |
| 4,221,803 | 9/1980 | Nardi et al. | 424/273 R |
| 4,248,881 | 2/1981 | Hoehn | 548/336 X |

Primary Examiner—Richard A. Schwartz
Attorney, Agent, or Firm—Jon S. Saxe; George M. Gould; John J. Maitner

[57] ABSTRACT

Imidazole compounds of the formula

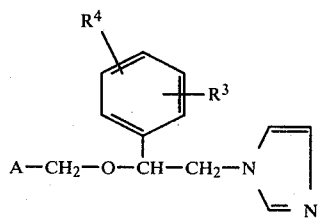

wherein A is a group of the formula

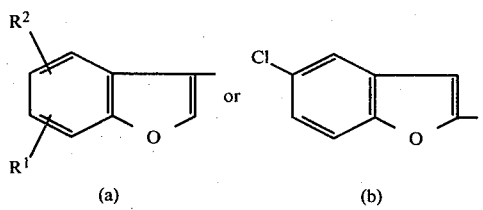

and $R^1$, $R^2$, $R^3$ and $R^4$ are each hydrogen or a halogen atom, pharmaceutically acceptable acid addition salts thereof, pharmaceutical compositions containing these compounds are described. The compounds of formula I are useful as antifungal agents. Processes for preparing the novel compounds are also disclosed.

18 Claims, No Drawings

ANTIFUNGAL BENZOFURANYL IMIDAZOLE COMPOUNDS

BRIEF SUMMARY OF THE INVENTION

The invention relates to imidazole compounds used in the treatment of fungal infections, and with the preparation of such compounds. The compounds of the invention are characterized by the formula

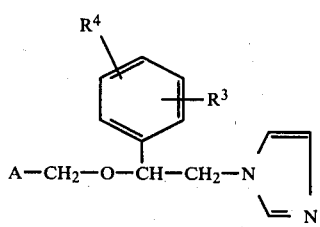
I wherein A is a group of the formula

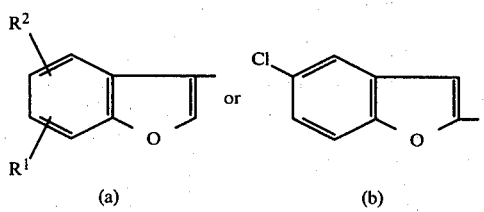

and $R^1, R^2, R^3$ and $R^4$ are each hydrogen or a halogen atom, and pharmaceutically acceptable acid addition salts thereof.

DETAILED DESCRIPTION OF THE INVENTION

The invention relates to imidazole compounds of the formula

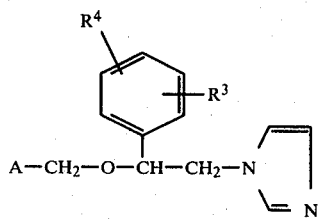
I wherein A is a group of the formula

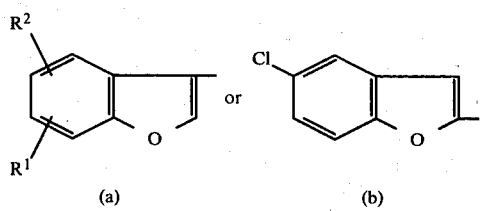

and $R^1, R^2, R^3$ and $R^4$ are each hydrogen or halogen atom, and pharmaceutically acceptable acid addition salts thereof.

As used herein, "halogen" denotes fluorine, chlorine, bromine or iodine.

In accordance with the invention, a preferred class of compounds are those compounds of formula I wherein A is a group of formula (a), $R^1$ is hydrogen or a halogen atom and $R^2$, $R^3$ and $R^4$ are each halogen, preferably chlorine, and pharmaceutically acceptable acid addition salts thereof.

Specifically preferred imidazole compounds falling with this class are:
1-[2,4-Dichloro-β-[(4,6-dichlorobenzofuran-3-yl)-methoxy]phenethyl]imidazole,
1-[2,4-dichloro-β-[(5,7-dichlorobenzofuran-3-yl)-methoxy]phenethyl]imidazole,
1-[2,4-dichloro-β-[(6-chlorobenzofuran-3-yl)-methoxy]phenethyl]imidazole and pharmaceutically acceptable acid addition salts thereof.

Another preferred class of imidazole compounds are those compounds of formula I wherein A is a group of formula (b) and $R^3$ and $R^4$ are each a halogen atom, preferably a chlorine atom, and pharmaceutically acceptable acid addition salts thereof.

Specifically preferred imidazole compounds falling within this class are:
1-[2,4-Dichloro-β-[(5-chlorobenzofuran-2-yl)methoxy]phenethyl]imidazole
and pharmaceutically acceptable acid addition salts thereof.

The imidazole compounds of formula I are prepared by reacting a compound of the formula $$A-CH_2-X \qquad II$$

wherein A has the meaning described above and X is chlorine or bromine,
with an alkali metal salt of an alcohol of the formula

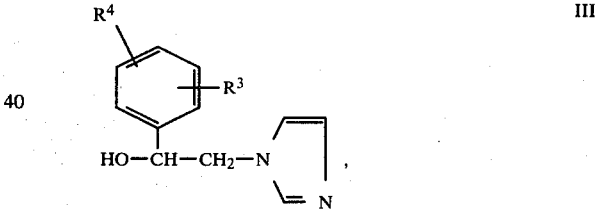
III wherein $R^3$ and $R^4$ have the meanings described above.

Many of the starting materials of formulas II and III are known compounds. Those compounds falling within the scope of formulas II and III which are not known can be conveniently prepared by methods analogous to the preparations of the known compounds given in the literature, or by methods described hereinafter.

The reaction of a compound of formula II with an alkali metal salt of an alcohol of formula III is conveniently carried out in the presence of a suitable solvent that is inert under the reaction conditions utilized as described hereinafter.

Suitable solvents for the above described reaction include aromatic hydrocarbons, such as benzene, toluene; ethers, such as 1,2-dimethoxyethane, tetrahydrofuran; and the like. A preferred solvent is dimethylformamide.

The reaction of the compounds of formulas II and III may be carried out at a temperature between about 0° C. and the boiling temperature of the reaction mixture. It is preferred to carry out the reaction however, at a temperature between about 0° C. and room temperature.

In an advantageous embodiment of the process of the present invention, a compound of formula II wherein X is bromine is reacted with the alkali metal salt of the alcohol of formula III. In this embodiment, the alkali metal salt of the alcohol of formula III is prepared in situ by treating the alcohol with an appropriate alkali metal base. Suitable alkali metal bases include, alkali metal hydride, such as, sodium hydride or an alkali metal amide, such as, sodium amide.

The starting materials of formula II wherein A is a group of formula (a) can be prepared as illustrated in the following Formula Scheme in which $R^1$, $R^2$ and X have the meanings described above:

Formula Scheme

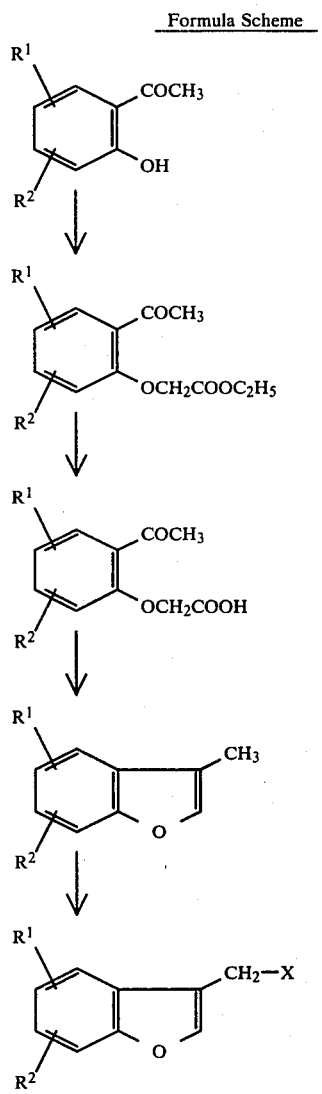

With reference to the foregoing Formula Scheme, in the first step a phenol of formula IV is converted into a compound of formula V employing known procedures. For example, reaction of ethyl bromoacetate in the presence of a base, such as, potassium carbonate, and in the presence of an inert organic solvent, such as, acetone.

In the second step, a compound of formula V is saponified to yield an acid of formula VI. The saponification can be carried out employing conventional procedures. For example, saponification is carried out using an alkali metal hydroxide, preferably sodium hydroxide.

An acid of formula VI is decarboxylated and cyclized in the third step to give a compound of formula VII. This decarboxylation and cyclization can be carried out employing conventional proceedures. For example, a compound of formula VI is treated acetic anhydride and sodium acetate at an elevated temperature.

Finally, in the fourth step a compound of formula VII is converted into a starting material of formula IIa by conventional chlorination or bromination procedures. For example, a compound of formula VII is treated with N-chlorosuccinimide or, preferably, N-bromosuccinimide, in carbon tetrachloride at an elevated temperature while irradiating the reaction.

The starting material of formula II wherein A is a group of formula (b) can be prepared, for example, by chlorinating or brominating 2-methyl-5-chlorobenzofuran. The chlorination or bromination of 2-methyl-5-chlorobenzofuran, which is a known compound, can be carried out in a manner analogous to that described above in connection with the conversion of a compound of formula VII into a starting material of formula IIa.

The imidazole compounds of formula I of this invention contain an asymmetric carbon atom and can exist as optical isomers or as racemates. It will be appreciated that the present invention includes within its scope the racemates and the optically active forms. If desired, a racemate can be resolved into the optical isomers according to procedures conventional known in the art for example, by fractional crystallization of salts with optically active acids.

The compounds of formula I may, depending on the process conditions utilized as described herein, be obtained as either the free base or in the form of acid addition salts. When it is desired to obtain the compounds of formula I in the form of their pharmaceutically acceptable acid addition salts, such salts are readily obtained by reaction of the free base with a suitable acid. Suitable acids include, for example, inorganic acids, such as, hydrochloric acid, sulfuric acid, hydrobromic acid, phosphoric acid and the like or organic acids, such as, citric acid, acetic acid, succinic acid, maleic acid, p-toluenesulfonic acid or the like. If desire, a salt of a compound of formula I can be converted into the free base or, if necessary, to a pharmaceutically acceptable salt by conventional procedures recognized in the art.

The imidazole compounds of formula I exhibit antifugal activity and are useful in the treatment of fungal infections. For such use the compounds of formula I or their pharmaceutically acceptable acid addition salts are administered as pharmaceutically acceptable compositions in combination with pharmaceutically, therapeutically inert inorganic or organic carrier materials suitable for enteral, topical or parenteral administration of medicaments. Such preparations may be in solid form, for example tablets, dragees, suppositories or capsules, in semi-solid form, for example, ointments, pastes or creams or may be in liquid form, that is solutions, suspensions or emulsions.

Suitable art-recognized therapeutically inert pharmaceutical carrier materials useful in the preparation of the compositions of the present invention include for example, water, gelatin, gum arabic, lactose, starch, talc, magnesium stearate, vegetable oil, polyalkyleneglycols and the like. The pharmaceutical compositions of the present invention may be sterilized and may contain art-recognized adjuvants, for example, preservatives, stabilizers, wetting or emulsifying agents, agents for flavor improvement, salts to adjust osmotic pressure, buffers and the like. Such compositions may likewise contain other therapeutically useful substances. The pharmaceutical compositions can be prepared by conventional procedures recognized in the art.

The imidazole compounds of formula I possess antifungal activity and are useful as antifungal agents. They are active against a wide variety of fungi which cause topical and systemic fungal infections as well as fungal infections of the mucuous membranes. For example, the compounds of formula I are active against *Candida albicans, Tricophyton mentagrophytes, Epidermophyton floccosum, Microsporum canis, Histoplasma capsulatum, Madurella mycetomi* and *Tricophyton quinckeanum.*

The in vitro antifungal activity of the imidazole compounds of formula I can be demonstrated in the following manner. A series of agar plates are treated with a standard culture of the microorganism and various concentrations of the test substance and the treated agar plates are then incubated at 37° C. for 7 days. Subsequently, the presence or absence of growth of the microorganism is evaluated and the Minimum Inhibitory Concentration (MIC) is determined. In this test, for example, 1-[2,4-dichloro-$\beta$-[(4,6-dichlorobenzofuran-3-yl)methoxy]phenethyl]imidazole nitrate has a MIC ($\mu$g/ml) of 10 against *Candida albicans,* 3 against *Tricophyton mentagrophytes* and less than 1 against *Epidermophyton floccosum* and *Microsporum canis.*

The in vivo antifungal activity of the imidazole compounds of formula I can be demonstrated in the following manner. Ovarectomised rats, maintained on estrogens, are vaginally infected with yeast cells of Candida albicans. The test substance is applied intravaginally in various concentrations in the form of a cream in polyethyleneglycol. The administration is effected twice daily on three consecutive days commencing 24 hours after the infection. Cultures are taken from each animal on the second, fourth and seventh day after the infection. The growing colonies are counted and the reduction in the number of colonies is calculated in comparison with control animals which are similarly infected but which are treated with polyethyleneglycol alone.

Compositions containing the imidazole compounds of formula I can be utilized in the therapeutic treatment of fungal infections in a considerable dosage range depending on the individual clinical condition. Generally, however, it is contemplated that the imidazole compounds of formula I may be administered to adults in an amount of from about 2 mg/kg to about 200 mg/kg for oral administration and in an amount of from about 0.5 mg/kg to about 50 mg/kg for parenteral administration. However, for any particular subject, the specific dosage regimen should be adjusted according to the individual need and the professional judgement of the person administering or supervising the administration of the aforesaid compound. It is to be understood that the dosages set forth herein are exemplary only and that they do not, to any extent, limit the scope or practice of this invention.

The following examples further illustrate the present invention.

EXAMPLE 1

A stirred solution of 0.51 g (0.002 mol) of 2,4-dichloro-$\alpha$-[(1-imidazolyl)methyl]benzyl alcohol was cooled to 0° C. and treated with 48 mg (0.002 mol) of sodium hydride (60 mg of an 80% dispersion in mineral oil). Stirring was continued and, after the effervescence had ceased (about 0.5 hour), the mixture was treated with a solution of 0.56 g (0.002 mol) of 3-bromomethyl-4,6-dichlorobenzofuran in 2 ml of dry dimethylformamide. The mixture was stirred at 0° C. for 0.5 hour and then at room temperature for 2 hours. The mixture was treated with 50 ml of water containing 0.5 ml of glacial acetic acid and then saturated with sodium chloride. The product was extracted with three 30 ml portions of ethyl acetate. The combined ethyl acetate extracts were washed with brine, dried over sodium sulphate and evaporated at 30° C./12 mmHg to give a pale brown viscous oil. This oil was dissolved in 15 ml of dry diethyl ether by the addition of the minimum volume of ethyl acetate and treated with 0.2 ml of concentrated nitric acid. The precipitated product was crystallised from ethanol to yield 0.57 g of 1-[2,4-dichloro-$\beta$-[(4,6-dichlorobenzofuran-3-yl)methoxy]-phenethyl]imidazole nitrate of melting point 105° C.

The 2,4-dichloro-$\alpha$-[(1-imidazolyl)methyl]benzyl alcohol used as the starting material can be prepared according to Godefroi et al, J. Med. Chem. 784,12, (1969).

The 3-bromomethyl-4,6-dichlorobenzofuran used as the starting material can be prepared as follows:

(a) A mixture of 10.25 g (0.05 mol) of 2-acetyl-3,5-dichlorophenol, 8.05 g (0.05 mol) of ethyl bromoacetate and 6.91 g (0.05 mol) of potassium carbonate in 150 ml of acetone was boiled under reflux for 3 hours. The mixture was filtered and the residue was washed with 50 ml of acetone. The filtrate and washings were combined and evaporated to give a viscous oil which was dissolved in 200 ml of methylene chloride and washed with water. The organic layer was dried over sodium sulphate and evaporated to give a red viscous oil which was purified by distillation to yield 13.1 g of ethyl 2-(2-acetyl-3,5-dichlorophenoxy) acetate of boiling point 180°-182° C./2 mmHg.

(b) A solution of 17.4 g (0.06 mol) of ethyl 2-(2-acetyl-3,5-dichlorophenoxy) acetate in 300 ml of ethanol was treated with a solution of 4.8 g (0.12 mol) of sodium hydroxide in 100 ml of water and the mixture was left to stand at room temperature for 18 hours. The ethanol was removed by evaporation and the solution remaining was acidified with 6 N hydrochloric acid. The mixture was extracted with three 75 ml portions of diethyl ether, the combined extracts were washed with brine, dried over sodium sulphate and evaporated to give 16.4 g of crued product. Recrystallization from methylene chloride/benzene yielded 14.4 g of pure 2-(2-acetyl-3,5-dichlorophenoxy) acetic acid of melting point 110° C.

(c) A mixture of 5.0 g (0.019 mol) of 2-(2-acetyl-3,5-dichlorophenoxy) acetic acid, 10.0 g of anhydrous sodium acetate and 50 ml of acetic anhydride was heated at 155° C. for 0.5 hour. The mixture was poured on to 100 g of ice and 100 ml of a saturated sodium bicarbonate solution. When decomposition of the excess acetic anhydride was complete, the mixture was extracted with three 100 ml portions of diethyl ether. The combined extracts were washed neutral with saturated sodium bicarbonate solution, dried over sodium sulphate and evaporated to give a brown oil which solidified on standing. The crude product was purified by distillation to yield 2.4 g of pure 4,6-dichloro-3-methylbenzofuran of boiling point 85° C./1 mmHg. The distilled product could be crystallized from petrol (boiling point 40°–60° C.) in the form of white needles of melting point 45° C.

(d) A solution of 2.01 g (0.01 mol) of 4,6-dichloro-3-methylbenzofuran in 50 ml of carbon tetrachloride was treated with 1.79 g (0.1 mol) of N-bromosuccinimide and the mixture was heated under reflux while irradiating with a 200 watt lamp. The reaction was complete after 1.5 hours (determined by thin-layer chromatography). The solution was left to cool and was then filtered. The filtrate was washed with 50 ml of sodium bicarbonate solution, dried over sodium sulphate and evaporated to give a brown oil. The oil was distilled in a Kugelrohr apparatus, to afford a cream colored oil which crystallized on standing (2.2 g). Crystallization from petroleum ether (boiling point 40° C.–60° C.) at 0° C. yielded 3-bromoethyl-4,6-dichlorobenzofuran in the form of cream colored needles of melting point 43° C.

EXAMPLE 2

In a manner analogous to that described in the first paragraph of Example 1, 1-[2,4-dichloro-β-[(5,7-dichlorobenzofuran-3-yl)methoxy]phenethyl]imidazole nitrate of melting point 132° C. was prepared by using 3-bromoethyl-5,7-dichlorobenzofuran in place of 3-bromoethyl-4,6-dichlorobenzofuran.

The 3-bromoethyl-5,7-dichlorobenzofuran used as the starting material was prepared from 2-acetyl-4,6-dichloro-phenol in a manner analogous to that described in Example 1(a)–(d) and melted at 68° C. [from petroleum ether (boiling point 40°–60° C.].

EXAMPLE 3

In a manner analogous to that described in the first paragraph of Example 1, 1-[2,4-dichloro-β-[(6-chlorobenzofuran-3-yl)methoxy]phenethyl]imidazole nitrate of melting point 154° C. is prepared by using 3-bromoethyl-6-chlorobenzofuran in place of 3-bromomethyl-4,6-dichlorobenzofuran.

The 3-bromomethyl-6-chlorobenzofuran used as the starting material was prepared from 2-acetyl-5-chloro-phenol in a manner analogous to that described in Example 1(a)–(d) and melted at 25° C. [from petroleum ether (boiling point 40°–60° C.)].

EXAMPLE 4

In a manner analogous to that described in the first paragraph of Example 1, 1-[2,4-dichloro-β-[(5-chlorobenzofuran-2-yl)-methoxy]phenethyl]imidazole nitrate of melting point 165° C. (from ethanol) is prepared by using 2-bromoethyl-5-chlorobenzofuran in place of 3-bromoethyl-4,6-dichlorobenzofuran.

The 2-bromomethyl-5-chlorobenzofuran used as the starting material can be prepared as follows:

2-Methyl-5-chlorobenzofuran, prepared in accordance with U.S. Pat. No. 2,559,532 was brominated in a manner analogous to that described in Example 1(d) to yield 2-bromomethyl-5-chlorobenzofuran of melting point 70° C. [from petroleum ether (boiling point 40°–60° C.)].

The following Example illustrates a typical pharmaceutical preparation containing the imidazole derivatives provided by the present invention:

EXAMPLE A

An ointment for topical administration containing the following ingredients can be prepared by conventional procedures.

| Ingredient | Parts by weight |
|---|---|
| Imidazole derivative | 2 |
| Propyleneglycol | 10 |
| Ointment base | 88 |
|  | 100 |

I claim:

1. A compound of the formula

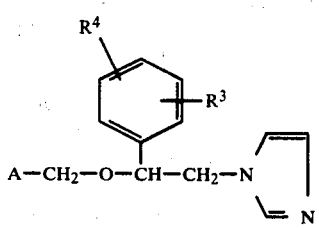

wherein A is a group of the formula

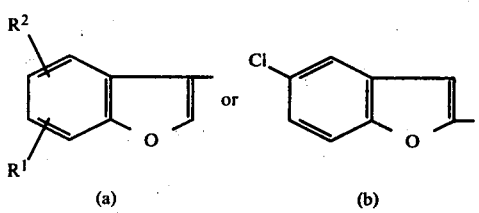

and $R^1, R^2, R^3$ and $R^4$ are each a hydrogen or halogen atom, or a pharmaceutically acceptable acid addition salt thereof.

2. A compound in accordance with claim 1, wherein A is the group of formula (a), or pharmaceutically acceptable acid addition salt thereof.

3. A compound in accordance with claim 2, wherein $R^1$ is hydrogen or a halogen atom and $R^2, R^3$ and $R^4$ are each a halogen atom.

4. A compound in accordance with claim 1, wherein A is the group of formula (b) and $R^3$ and $R^4$ are each a halogen atom, or a pharmaceutically acceptable acid addition salt thereof.

5. A compound in accordance with claim 1, 1-[2,4-Dichloro-β-[4,6-dichlorobenzofuran-3-yl)-methoxy]-phenethyl]imidazole or a pharmaceutically acceptable acid addition salt thereof.

6. A compound in accordance with claim 1, 1-[2,4-Dichloro-β-[5,7-dichlorobenzofuran-3-yl)-methoxy]-phenethyl]imidazole or a pharmaceutically acceptable acid addition salt thereof.

7. A compound in accordance with claim 1, 1-[2,4-Dichloro-β-[(6-chlorobenzofuran-3-yl)-methoxy]-phenethyl]imidazole or a pharmaceutically acceptable acid addition salt thereof.

8. A compound in accordance with claim 1, 1-[2,4-Dichloro-β-[(5-chlorobenzofuran-2-yl)methoxy]-phenethyl]imidazole or a pharmaceutically acceptable acid addition salt thereof.

9. A pharmaceutical composition for the treatment of fungal infections comprising a therapeutically inert carrier and an effective amount of a compound of the formula

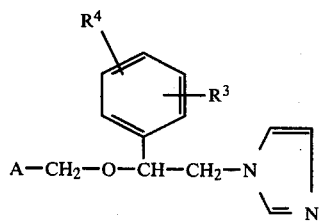

wherein A is a group of the formula

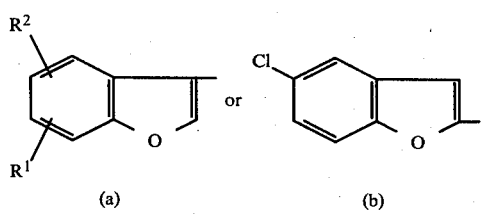

and $R^1, R^2, R^3$ and $R^4$ are each a hydrogen or halogen atom,
or a pharmaceutically acceptable acid addition salt thereof.

10. A pharmaceutical composition in accordance with claim 9 wherein the compound of formula I is 1-[2,4-Dichloro-β-[(4,6-dichlorobenzofuran-3-yl)-methoxy]phenethyl]imidazole or a pharmaceutically acceptable acid addition salt thereof.

11. A pharmaceutical composition in accordance with claim 9 wherein the compound of formula I is 1-[2,4-Dichloro-β-[(5,7-dichlorobenzofuran-3-yl)-methoxy]phenethyl]imidazole or a pharmaceutically acceptable acid addition salt thereof.

12. A pharmaceutical composition in accordance with claim 9 wherein the compound of formula I is 1-[2,4-Dichloro-β-[(6-chlorobenzofuran-3-yl)-methoxy]phenethyl]imidazole or a pharmaceutically acceptable acid addition salt thereof.

13. A pharmaceutical composition in accordance with claim 9 wherein the compound of formula I is 1-[2,4-Dichloro-β-[(5-chlorobenzofuran-2-yl)methoxy]-phenethyl]imidazole or a pharmaceutically acceptable acid addition salt thereof.

14. A method for the treatment of fungal infections which comprises administering to a host requiring such treatment an amount effective therefor of a compound of the formula

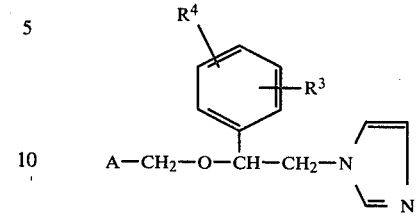

wherein A is a group of the formula

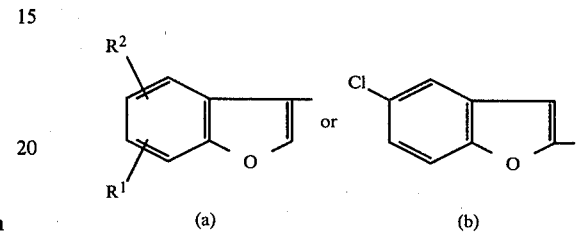

and $R^1, R^2, R^3$ and $R^4$ are each a hydrogen or halogen atom,
or a pharmaceutically acceptable acid addition salt thereof.

15. A method in accordance with claim 14 wherein the compound of formula of formula I is 1-[2,4-Dichloro-β-[(4,6-dichlorobenzofuran-3-yl)-methoxy]-phenethyl]imidazole or a pharmaceutically acceptable acid addition salt thereof.

16. A method in accordance with claim 14 wherein the compound of formuula I is 1-[2,4-Dichloro-β-[(5,7-dichlorobenzofuran-3-yl)-methoxy]phenethyl-]imidazole or a pharmaceutically acceptable acid addition salt thereof.

17. A method in accordance with claim 14 wherein the compound of formula I is [2,4-Dichloro-β-[(6-chlorobenzofuran-3-yl)-methoxy]phenethyl]imidazole or a pharmaceutically acceptable acid addition salt thereof.

18. A method in accordance with claim 14 wherein the compound of formula I is 1-[2,4-Dichloro-β-[(5-chlorobenzofuran-2-yl)methoxy]-phenethyl]imidazole or a pharmaceutically acceptable acid addition salt thereof.

* * * * *